United States Patent [19]

Morrison

[11] Patent Number: 5,125,133
[45] Date of Patent: Jun. 30, 1992

[54] OSTOMY POUCH CLAMP WITH HINGE-SUPPLEMENTING GUIDE BLADE

[75] Inventor: William Morrison, Ontario, Canada

[73] Assignee: Hollister Incorporated, Libertyville, Ill.

[21] Appl. No.: 796,655

[22] Filed: Nov. 25, 1991

[51] Int. Cl.⁵ .......................... B65D 77/10; A61F 5/44
[52] U.S. Cl. ............................ 24/30.5 R; 24/30.5 P; 24/518; 604/335
[58] Field of Search ........... 24/30.5 R, 30.5 P, 30.5 S, 24/30.5 W, 30.5 L, 30.5 T, 517, 518, 498, 570; 604/335

[56] References Cited

U.S. PATENT DOCUMENTS

| | | | |
|---|---|---|---|
| 381,265 | 4/1888 | Martens | 24/30.5 R |
| 3,036,506 | 5/1962 | Andresen, Jr. | 24/30.5 R |
| 3,523,534 | 8/1970 | Nolan | 604/335 |
| 3,669,115 | 6/1972 | Melges | 24/518 |
| 4,275,485 | 6/1981 | Hutchison | 24/30.5 R |
| 4,296,529 | 10/1981 | Brown | 24/30.5 P |
| 4,551,888 | 11/1985 | Beecher | 24/30.5 |
| 4,834,730 | 5/1989 | Holtermann et al. | 604/335 |
| 4,887,335 | 12/1989 | Folkmar | 24/30.5 |
| 4,983,172 | 1/1991 | Steer et al. | 604/332 |
| 5,050,272 | 9/1991 | Robinson et al. | 24/30.5 R |

OTHER PUBLICATIONS

Instructions for using the Hollister Premium Drainable Pouch Clamp (product literature published 1984), (one sheet).

*Primary Examiner*—Victor N. Sakran
*Attorney, Agent, or Firm*—Tilton Fallon Lungmus

[57] ABSTRACT

A one-piece plastic clamp for closing the lower end of a drainable ostomy pouch, the clamp being similar to prior constructions in having a thin wedge member receivable in the channel of narrow trough member for clamping the outlet end of a collection pouch in folded and sealed condition. The two members have adjacent ends joined by a flexible hinge strap, and the end of the wedge member below the strap has a thin, integral guide blade projecting endwise therefrom. The guide blade is receivable in, and extendable through, a slit-like opening in the corresponding end of the trough member for guiding the closing of the clamp and for tightly maintaining the ends of the members together even if the hinge strap should become damaged in use.

12 Claims, 1 Drawing Sheet

U.S. Patent June 30, 1992 5,125,133
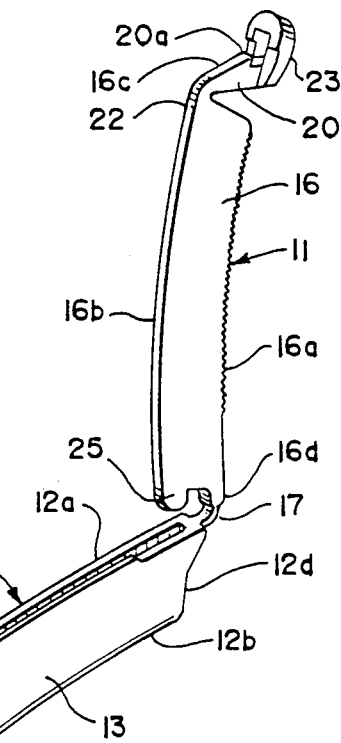
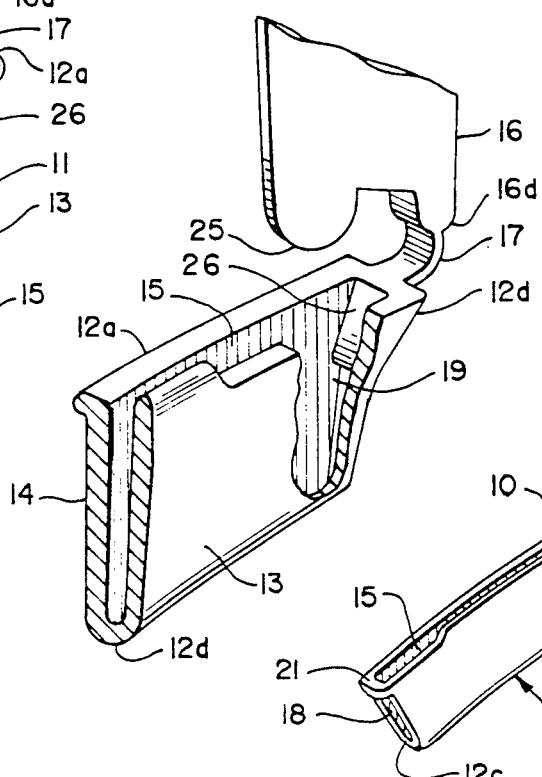
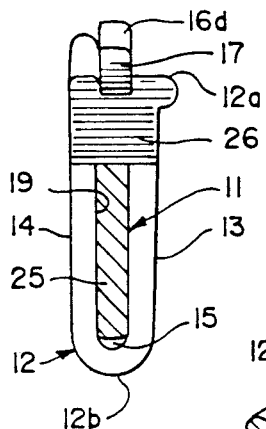
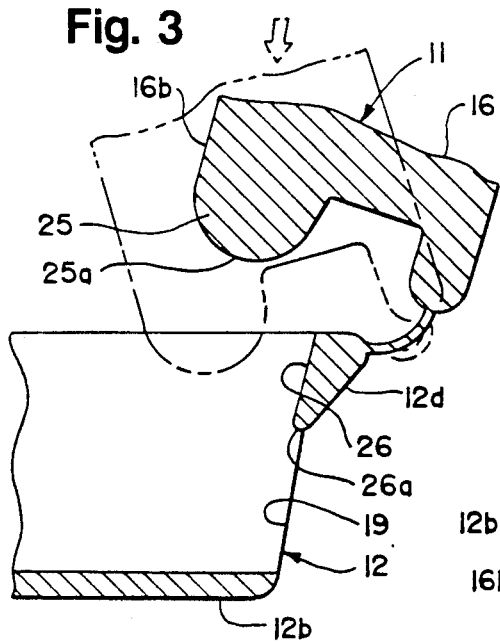
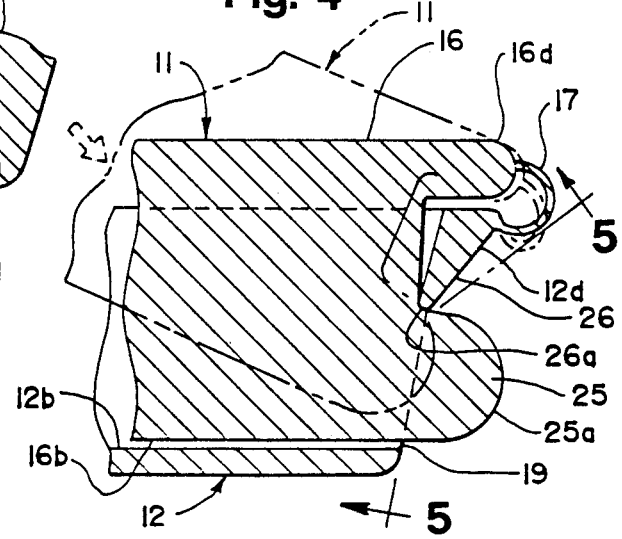

OSTOMY POUCH CLAMP WITH HINGE-SUPPLEMENTING GUIDE BLADE

BACKGROUND AND SUMMARY

Nolan U.S. Pat. No. 3,523,534 discloses a clamp 36 for a drainable ostomy pouch 10, the clamp having a thin wedge member 40 and a channel-defining trough member 38. The two parts are hinged together at one end of the clamp and, at the clamp's opposite end, have a latch 46, 52 for securing the members in closed condition. While the members are generally planar, they preferably have a slight longitudinal curvature to conform with the contour of the patient's body as indicated generally in FIGS. 1 and 3. In use, the lower end of a pouch is reversely folded about the lower edge of the blade-like wedge member 40 (FIG. 5) and the clamp is then closed to seal the folded end portion of the pouch in the channel (FIG. 4).

In the aforementioned patent, the wedge and trough members are separate elements that are connected together by a hook-like hinge member 50; however, similar products have been marketed by the patentee with an integral and flexible strap hinge joining the members together. In either case, when such a clamp is fully opened, the hinge means allows a wide range of relative twisting movement of the parts. Once such a clamp is closed, the latching means at one end securely locks the members together at that end of the clamp. At the clamp's opposite end, however, the members are essentially held together by the hinge. While the likelihood of damage to such a hinge may not be great, should such damage occur, to the extent that the hinge connection is broken, forceable separation of the members and release of the clamp would be possible.

Accordingly, an important aspect of this invention lies in providing an improved clamp having a thin, blade-like extension at the hinge end of the wedge member for the plural purposes of guiding the members as the clamp is being closed and for reinforcing the hinge and holding the members together even if the hinge should somehow rupture or break in use.

Briefly, the improvement comprises a thin, integral guide blade that is generally coplanar with the wedge member and extends in an endwise direction from one end of that member. The guide blade is spaced below the hinge and has a smoothly curved peripheral edge that merges with the bottom edge of the wedge member. Particularly effective results are achieved if the curved peripheral edge is generally semi-circular in outline.

The guide blade is received in a slit-like end opening of the trough member. The upper limits of that opening are defined by a end wall that bridges the channel of the trough member and provides bearing means for engaging the guide blade and for camming the end of the wedge member into the channel during the final stages of a clamping operation.

Other features, advantages, and objects of the invention will become apparent from the specification and drawings.

DRAWINGS

FIG. 1 is a perspective view of a pouch clamp embodying this invention, the clamp being shown in open condition.

FIG. 2 is an enlarged fragmentary perspective view similar to FIG. 1 but with a wall portion of the trough member cut away to illustrate structural features of the clamp.

FIG. 3 is a fragmentary longitudinal sectional view showing the hinged end of the clamp with the clamp shown in fully opened condition (solid lines) and in an early stage of closing (broken lines).

FIG. 4 is a sectional view similar to FIG. 3 but showing the clamp in partially closed condition (broken lines) and in fully closed condition (solid lines).

FIG. 5 is a cross sectional view taken along line 5—5 of FIG. 4.

DETAILED DESCRIPTION OF PREFERRED EMBODIMENT

Referring to the drawings, numeral 10 designates a clamp of the general type disclosed in aforementioned U.S. Pat. No. 3,523,534. The clamp includes a thin, elongate, generally-planar wedge member 11 and a narrow, channel-defining trough member 12. The trough member includes side walls 13 and 14 that are spaced apart to define channel 15 therebetween. As shown in the drawings, the trough member is generally U-shaped in cross section, is open at its top 12a, closed along its bottom 12b, and has a pair of opposite ends 12c, 12d.

The wedge member 11 has a thin, elongate body 16 with generally parallel longitudinal (upper and lower) edges 16a and 16b, and opposite ends 16c and 16d. End 16d is joined to end 12d of the trough member by hinge means in the form of a thin, narrow, flexible hinge strap 17. The hinge strap is integrally formed with the members 11 and 12 of the one-piece clamp. While that clamp is formed of a relatively rigid or stiff plastic material such as polyethylene or polypropylene, strap 17 is nevertheless highly flexible and deformable because of its narrowness and thinness. Such flexibility also means that when the clamp is open, as shown in FIGS. 1 and 2, there is the possible disadvantage that the wedge member 11 may be easily twisted out of alignment with trough member 12. While it is deemed highly advantageous to form the clamp in one piece, utilizing a flexible hinge strap 17 as shown and described, it will be understood that the clamp might alternatively be formed in two pieces using, for example, a hook-type hinge as disclosed in U.S. Pat. No. 3,523,534. Even in such a construction, sufficient flexibility or play would exist in the hinge to permit the wedge member to be shifted out of alignment with the trough member when the clamp is open.

As shown clearly in FIGS. 1 and 2, ends 12c and 12d of the trough member 12 are provided with slit-like openings 18 and 19, respectively. Opening 18 cooperates with the integral latch element 20 at end 16c of the body 16 of the wedge member. The latch element or arm 20 tapers forwards the lower edge 16b of the body and has a shoulder 20a that engages a lip 21 extending across and closing off the upper limits of opening 18. When the clamp is closed, latch arm 20 engages the lip and flexes inwardly about its point of connection 22 to the remainder of the body 16. As soon as shoulder 20a clears lip 21, the latch arm springs back towards its original position to hold the members 11 and 12 in latched condition. Enlargement 23 at the free end of latch arm 20 serves as a lever for urging arm 20 into unlatching position when opening of the clamp is desired. The structure so far described is generally similar to products that have been commercially available for a number of years. Unlike such prior products, however, the clamp of this invention includes a thin, integral guide blade 25 that extends in an endwise direction from end 16d of wedge member 11. The guide blade extension has a smoothly-curved peripheral edge 25a of generally semi-circular outline that merges smoothly with the lower edge 16b of wedge body 16. The guide blade is spaced well below the point of attachment between hinge 17 and end 16d of the body and, when the clamp is closed, the guide blade extends into and through slit-like opening 19 in trough member 12.

Opening 19 is bridged at its upper end by an end wall 26 that is formed integrally with side walls 13, 14 and that also serves as the area of connection for hinge strap 17. End wall 26 has a rounded lower edge surface 26a that serves as a bearing surface for camming the wedge member 11 downwardly when it engages the arcuate edge 25a of guide blade 25, as depicted in broken lines in FIG. 4. For such camming action to occur, the parts must be dimensioned so that the guide blade 25 is spaced below the upper corner of wedge member 11, and the area of connection with hinge strap 17, a distance greater than the vertical dimension of end wall 26.

As shown most clearly in FIG. 5, the width of guide blade 25, and the width of the wedge body 16 of which it is an integral part, is the same or slightly less than the width of channel 15. When the drainage end of a pouch is reversely folded about edge 16b in the manner shown and described in the aforementioned patent, and the clamp is then closed, the material of the pouch becomes tightly clamped in the channel, thereby sealing the pouch against leakage through the drainage opening. However, as stated above, hinge 17 allows considerable freedom of movement of the wedge member 11 when the clamp is open. The guide blade 25 is the first part of the wedge member to enter channel 15 as the clamp is being closed (note the structure shown in broken lines in FIG. 3), with the result that the guide blade performs a significant function in properly orienting and guiding members 11 and 12 as closing of the clamp commences. When the wedge member 11 reaches the partially closed position shown in broken lines in FIG. 4, arcuate surface 25a of the guide blade bears against camming surface 26a of the end wall to direct the wedge member downwardly into seated position within the channel. Finally, when the clamp is fully closed, as depicted in solid lines in FIG. 4, the guide blade 25 protrudes through slit-like opening 19 and effectively limits upward movement of the wedge member. Even if hinge strap 17 should become damaged or broken in use, the guide blade 25 will insure that the clamp remains in closed condition until such time as the latch 20 is intentionally released and the wedge member is pivoted into a raised position.

While in the foregoing, I have disclosed an embodiment of the invention in considerable detail for purposes of illustration, it will be understood by those skilled in the art that many of these details may be varied without departing from the spirit and scope of the invention.

I claim:

1. A clamp for closing the lower end of a drainable ostomy pouch, said clamp comprising a wedge member having a thin, elongate body with generally parallel upper and lower edges and a pair of opposite ends; a mating, narrow, U-shaped trough member having an open top, a closed bottom, and a pair of opposite ends; one of said ends of said trough member having a slit-like opening bridged by an integral end wall; and strap means joining said end wall of said trough member and one of said ends of said wedge member adjacent said upper edge thereof; wherein the improvement comprises
said one end of said wedge member including a thin, integral guide blade extending endwise therefrom; said guide blade being dimensioned to be slidably received by said trough member and extendable into and through said slit-like opening for guiding the closing of said clamp and for securing said members against unintentional separation should said hinge means become damaged during use of said clamp.

2. The clamp of claim 1 in which said thin body is generally planar and said guide blade is coplanar therewith.

3. The clamp of claims 1 or 2 in which said guide blade is disposed adjacent said lower edge of said wedge member and has a smoothly curved peripheral edge.

4. The clamp of claim 3 in which said peripheral edge is generally semi-circular in outline.

5. The clamp of claims 1 or 2 in which said end wall of said trough member is engagable with said guide blade as said clamp is closed for camming the ends of said members adjacent said hinge strap into close mating engagement.

6. The clamp of claims 1 or 2 in which said members each has a slight and gradual longitudinal curvature throughout the length thereof.

7. A one-piece clamp of semi-rigid plastic material for closing the lower end of a drainable ostomy pouch, said clamp comprising a wedge member having a thin, elongate body with generally parallel upper and lower edges and a pair of opposite ends; a mating, narrow, U-shaped trough member having an opened top, a closed bottom, and a pair of opposite ends; one of said ends of said trough member having a slit-like opening bridged adjacent the top of said trough member by an integral end wall; and a flexible hinge strap integrally joining said end wall of said trough member and one of said ends of said wedge member adjacent said upper edge thereof; wherein the improvement comprises
said one end of said wedge member including a thin, integral guide blade extending therefrom; said guide blade being disposed adjacent said lower edge of said wedge member and being dimensioned to be slidably received by said trough member and extendable into and through said slit-like opening for guiding the closing of said clamp and for securing said members against unintentional separation.

8. The clamp of claim 7 in which said body is generally planar and said guide blade is coplanar therewith.

9. The clamp of claim 8 in which said guide blade has a smoothly curved peripheral edge.

10. The clamp of claim 9 in which said peripheral edge is generally semi-circular in outline.

11. The clamp of claim 7 in which said end wall of said trough member is engagable with said guide blade as said clamp is closed for camming the ends of said members adjacent said hinge strap into close mating engagement.

12. The clamp of claim 7 in which said members each has a slight and gradual longitudinal curvature throughout the length thereof
* * * * *